United States Patent [19]

Fuchikami et al.

[11] Patent Number: 4,855,487

[45] Date of Patent: Aug. 8, 1989

[54] PROCESS FOR PREPARING FLUORINE-CONTAINING CARBOXYLIC ACID ESTER

[75] Inventors: Takamasa Fuchikami; Hisao Urata; Yoshimitsu Ishii, all of Kanagawa, Japan; Yoshiko Obata, Rockville, Md.

[73] Assignee: Sagami Chemical Research Center, Tokyo, Japan

[21] Appl. No.: 71,832

[22] Filed: Jul. 10, 1987

[30] Foreign Application Priority Data

Jul. 11, 1986 [JP] Japan ................................ 61-161915
Dec. 19, 1986 [JP] Japan ................................ 61-301332

[51] Int. Cl.$^4$ .................... C07C 69/63; C07C 69/635; C07C 51/10
[52] U.S. Cl. .................................... 560/227; 560/226; 562/520
[58] Field of Search ................ 560/227, 226; 562/520

[56] References Cited

U.S. PATENT DOCUMENTS

| 3,790,607 | 2/1974 | Lichstein | 560/227 |
| 4,582,929 | 4/1986 | De Vries | 562/520 |
| 4,713,484 | 12/1987 | Epstein | 562/520 |

OTHER PUBLICATIONS

Fuchikami et al., *J. Org. Chem.*, 1983, vol. 48, 3803–3807.

*Primary Examiner*—Donald B. Moyer
*Assistant Examiner*—Julie K. Parker
*Attorney, Agent, or Firm*—Sughrue, Mion, Zinn, Macpeak, and Seas

[57] ABSTRACT

An improved process for preparing a fluorine-containing carboxylic acid ester useful as an intermediate for producing a fluorine-containing carboxylic acid is disclosed. The process comprises reacting a fluorine-containing alkyl halide with carbon monoxide and an alcohol in the presence of a transition metal catalyst of the Group VIII of the Periodic Table and a base, and provides the desired carbonylated compound in high yield.

6 Claims, No Drawings

PROCESS FOR PREPARING FLUORINE-CONTAINING CARBOXYLIC ACID ESTER

FIELD OF THE INVENTION

This invention relates to a process for preparing a fluorine-containing carboxylic acid ester. More specifically, this invention relates to a novel process for preparing a fluorine-containing carboxylic acid ester represented by the formula (I)

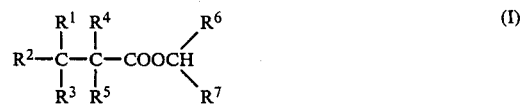

wherein $R^1$ represents a fluorine atom or a polyfluorocarbon group, $R^2$ and $R^3$ each represents a hydrogen atom, a fluorine atom, an alkyl group, an aralkyl group, an alkenyl group or an aryl group, $R^4$, $R^5$, $R^6$ and $R^7$ each represents a hydrogen atom, an alkyl group, an aralkyl group, an alkenyl group or an aryl group, and $R^2$ and $R^3$, $R^2$ and $R^4$, $R^3$ and $R^5$, $R^4$ and $R^5$, or $R^6$ and $R^7$, when taken together with the carbon atom(s) to which they are attached, can form a ring.

BACKGROUND OF THE INVENTION

At present, fluorine-containing carboxylic acids are used for a wide variety of utilities such as surface active agents or surface treating agents because of their excellent stability, chemical resistance, weather resistance, water- and oil-repellency, and are also useful as intermediates for the synthesis of physiologically active substances. The fluorine-containing carboxylic acid esters obtained by the process of this invention are important intermediates for the synthesis of various useful compounds having the above-described properties.

Typical conventional processes for preparing fluorine-containing carboxylic acid ester derivatives comprise the Reppe method using a fluorine-containing substituted ethylene. Examples of the conventional processes include (1) a process comprising reacting a perfluorooctylethylene with carbon monoxide at 380 atms. in ethanol in the presence of a palladium catalyst and an alcoholic hydrogen chloride at a temperature of 140° C. for 7 hours to obtain a mixture of ethyl α- and β-perfluorooctylpropionate, as described in German OLS No. 2137712; (2) a process comprising reacting trifluoropropene with an alcohol in the presence of a divalent palladium catalyst having a tertiary phosphine ligand under a carbon monoxide pressure of 110 atms. at a temperature of from 100° to 125° C. for a period of from 30 to 70 hours to obtain a mixture of ethyl α- and β-trifluoromethylpropionate, as described in T. Fuchikami, K. Ohishi and I. Ojima, J. Org. Chem., Vol. 48, 3803 (1983), etc. However, each of the above conventional processes (1) and (2) is not advantageous in that the selectivity to the position of carbon atom where carbonylation occurs is low. That is, although ethyl β-perfluoroalkyl propionate is produced preferentially, an α-substituted product is also produced in a substantial amount, and these products are difficult to separate into respective pure product. Further, the above conventional processes require a carbon monoxide pressure higher than 100 atms. and, hence, are very expensive in order to secure safety of the process.

As a result of extensive studies for overcoming the disadvantages of the conventional processes, the present inventors found that a single carbonylated product, i.e., a fluorine-containing carboxylic acid ester represented by the formula (I) can be produced in high yield according to the process of this invention.

DETAILED DESCRIPTION OF THE INVENTION

This invention relates to a process for preparing a fluorine-containing carboxylic acid ester represented by the formula (I)

wherein $R^1$ represents a fluorine atom or a polyfluorocarbon group, $R^2$ and $R^3$ each represents a hydrogen atom, a fluorine atom, an alkyl group, an aralkyl group, an alkenyl group or an aryl group, $R^4$, $R^5$, $R^6$ and $R^7$ each represents a hydrogen atom, an alkyl group, an aralkyl group, an alkenyl group or an aryl group, and $R^2$ and $R^3$, $R^2$ and $R^4$, $R^3$ and $R^5$, $R^4$ and $R^5$, or $R^6$ and $R^7$, when taken together with the carbon atom(s) to which they are attached, can form a ring, which comprises reacting a fluorine-containing alkyl halide represented by the formula (II)

wherein $R^1$, $R^2$, $R^3$, $R^4$ and $R^5$ are as defined above, and X represents an iodine atom, a bromine atom or a chlorine atom, with carbon monoxide and an alcohol represented by the formula (III)

$$\begin{array}{c} H \\ | \\ R^6-C-OH \\ | \\ R^7 \end{array} \quad (III)$$

wherein $R^6$ and $R^7$ are as defined above, in the presence of a transition metal catalyst of the Group VIII of the Periodic Table and a base.

The term "alkyl group" as used herein means a straight or branched chain alkyl group having 1 to 10 carbon atoms or a cycloalkyl group having 3 to 10 carbon atoms.

The term "alkenyl group" as used herein means an alkenyl group having 2 to 10 carbon atoms.

The term "aryl group" as used herein means a phenyl or naphthyl group, or a phenyl group substituted with at least one of halogen atoms, alkyl, alkoxy, hydroxy, nitro, acyl, acyloxy and amino groups.

The term "aralkyl group" as used herein means an aralkyl group having the above aryl moiety and an alkyl group having 1 to 10 carbon atoms.

In the process of this invention, it is essential to conduct the reaction in the presence of a transition metal catalyst of the Group VII of the Periodic Table. The transition metal catalysts which can be used include a metal of iron, ruthenium, osmium, cobalt, rhodium, iridium, nickel, palladium or platinum; a metal salt, a metal complex compound, an organometallic complex containing a halogen atom ligand, an organometallic complex containing a tertially phosphine ligand, and an organometallic complex containing an olefin or acetylene compound as a ligand of the above metal, as well as the above transition metal or metal compound of the Group VIII supported on a carrier such as silica gel, alumina, etc.

Suitable examples of the catalyst include iron carbonyl, ruthenium carbonyl, osmium carbonyl, nickel carbonyl, iron chloride, cobalt chloride, ruthenium chloride, rhodium chloride, nickel chloride, palladium chloride, platinum chloride, dichlorobis(triphenylphosphine)nickel, dichlorobis(triphenylphosphine)palladium, dichloro(1,2-bisphenylphosphinoethane)palladium, dichloro(1,3-bis-diphenylphosphinopropane)palladium, dichloro(1,4-bisdiphenylphosphinobutane)palladium, dichloro(1,1′-bisdiphenylphosphinoferrocene)palladium, dichlorobis(diphenylmethylphosphine)palladium, dichlorobis(triphenylphosphine)palladium, bis(cyclooctadiene)nickel, dichloro(cyclooctadiene)palladium, tetrakis(triphenylphosphine)nickel, chlorotris(triphenylphosphine)rhodium, chlorotris(triphenylphosphine)iridium, chlorocarbonylbis(triphenylphosphine)rhodium, chlorocarbonylbis(triphenylphosphine)iridium, tetrakis(triphenylphosphine)palladium, tetrakis(triphenylphosphine)platinum and the like.

The transition metal catalyst of the Group VIII can be used in an amount of from about b 1/10000 to about 1/5 molar equivalent to the fluorine-containing alkyl halide of the formula (II), preferably, 1/500 to 1/5 molar equivalent to the compound of formula (II).

The process according to the present invention is carried out in the presence of a base. Examples of bases which can be used in the present invention include inorganic bases such as hydrides, hydroxides, carbonates, bicarbonates or carboxylates of alkali metals or alkaline earth metals; alkali metal alkoxides, alkali metal amides and the like; tertiary amines such as triethylamine, tri(isobutyl)amine, N,N-dimethylaniline and the like; and aromatic amines such as pyridine, 2,6-lutidine and the like. The base can be used in an amount of from about 0.5 to about 5 molar equivalent to the fluorine-containing alkyl halide of the formula (II).

The fluorine-containing alkyl halides represented by the formula (II) used as a starting material of this invention are easily available as commercial products, and examples of the alkyl halides include 1,1,1-trifluoro-2-iodoethane, 1,1,1-trifluoro-2-bromoethane, 1,1,1trifluoro-2-chloroethane, 1,1,1-trifluoro-3-iodopropane, 1,1,1-trifluoro-3-bromopropane, 1,1,1-trifluoro-3-chloropropane, 1-fluoro-2-iodopropane, 1-perfluoroethyl-2-iodoethane, 1-perfluoroethyl-2-bromoethane, 1-perfluoroethyl-2-chloroethane, 1-perfluoropropyl-2-iodoethane, 1-perfluoroisopropyl-2-iodoethane, 1-perfluorobutyl-2-iodoethane, 1-perfluoropentyl-2-iodoethane, 1-perfluorohexyl-2-iodoethane, 1-perfluoroheptyl-2-iodoethane, 1-perfluorooctyl-2-iodoethane, 1-perfluorodecyl-2-iodoethane, 1-perfluorocyclohexyl-2-iodoethane, 1-perfluoropropyl-2-bromoethane, 1-perfluoroisopropyl-2-bromoethane, 1-perfluorobutyl-2-bromoethane, 1-perfluoropentyl-2-bromoethane, 1-perfluorohexyl-2-bromoethane, 1-perfluoroheptyl-2-bromoethane, 1-perfluorooctyl-2-bromoethane, 1-perfluorodecyl-2-bromoethane, 1-trifluoromethyl-2-iodopropane, 1-perfluoroethyl-2-iodopropane, 1-perfluoropropyl-2-iodopropane, 1-perfluorobutyl-2-iodopropane, 1-perfluorohexyl-2-iodopropane, 1-perfluoroheptyl-2-iodopropane, 1-perfluorooctyl-2-iodopropane, 1-perfluorodecyl-2-iodopropane, 1-trifluoromethyl-2-iodobutane, 1-perfluoroethyl-2-iodobutane, 1-perfluoropropyl-2-iodobutane, 1-perfluorobutyl-2-iodobutane, 1-perfluorohexyl-2-iodobutane, 1-perfluorooctyl-2-iodobutane, 1-trifluoromethyl-2-iodopentane, 1-perfluoroethyl-2-iodopentane, 1-perfluoropropyl-2-iodopentane, 1-perfluorobutyl-2-iodopentane, 1-perfluorohexyl-2-iodopentane, 1-perfluorooctyl-2-iodopentane, 1-perfluoroethyl-2-iodohexane, 1-perfluorobutyl-2-iodohexane, 1-perfluorohexyl-2-iodohexane, 1-perfluorooctyl-2-iodohexane, 1-perfluorooctyl-2-iodooctane, 1-perfluorohexyl-2-iodooctane, 1-perfluorooctyl-2-iodocyclohexane, 1-perfluorohexyl-2-iodocyclopentane, 5-iodo-6-perfluorooctyl-2-hexanone, 1-perfluorobutyl-2-iodo-3-phenylpropane, 1-perfluorohexyl-2-iodo-7-octene, 1-perfluoroheptyl-2-bromo-9-decene, 1-perfluorononyl-2-chloro-5-hexene, 1-(3-cyclohexenyl)-1-iodoperfluorobutylethane, 1-perfluorohexylmethyl-1-iodocyclohexane, 1-(2,2,2-trifluoroethyl)-1-bromocyclohexane, 1-perfluorooctylmethyl-1-chlorocyclopentane, 1-perfluorobutylmethyl-1-iodo-4-cyclooctene, 1-iodomethyl-1-perfluoroethylcyclohexane, 1-bromomethyl-1-perfluorodecylcyclooctane, 1-chloromethyl-1-trifluoromethylcyclopentane, -perfluorooctyl-2-bromo-3-phenylpropane, 1-iodo-1-trifluoromethyl-4-phenyl-3-propene, 1-perfluoroobutyl-2-iodo-4-methylhexane, 1-perfluorohexyl-2-iodo-4-methylhexane, 1-perfluoroexyl-2-iodo-4-methylhexane, 1-perfluoropropyl-2-ethyl-2-iodohexane, 1-perfluoroisopropyl-2-iodo-2,4-dimethylhexane, 1-perfluorobutyl-2-iodo-2-cyclohexylethane, 1-trifluoromethyl-2-iodo-2-cyclohexylethane, 1-perfluoroethyl-2-iodo-2-cyclohexylethane, 1-perfluorooctyl-2-iodo-2-cyclohexylethane, 1-trifluoromethyl-2-iodo-2-cyclopentylethane, 1-perfluoropropyl-2-iodo-2-cyclopentylethane, 1-perfluorohexyl-2-iodo-2-cyclopentylethane, and the like.

The alcohols represented by the formula (III) which can be used in the present invention include straight or branched chain or cyclic alcohols such as methanol, ethanol, propanols, butanols, pentanols and hexanols; benzyl alcohol, 2-penyl-1-ethanol, furfuryl alcohol, 3-butene-1-ol and the like.

The alcohol is preferably used in an amount of at least an equimolar amount to the fluorine-containing alkyl halide represented by the formula (II), and any excess amount of the alcohol can be used so as to serve as a diluent.

The process according to the present invention is carried out in an atmosphere of carbon monoxide which may be diluted with an inert gas such as argon, nitrogen and the like.

The reaction proceeds efficiently under a carbon monoxide partial pressure below about 50 atms., but a higher pressure can be used, if desired.

In carrying out the process of this invention, an inert solvent which does not take part in the reaction may be additionally used, if desired. A preferred solvent includes that forms a single reaction phase, but the solvent which forms a second liquid phase in the reaction mixture may also be used. Examples of solvents which can be preferably used include hydrocarbon solvents such as hexane, heptane, cyclohexane, benzene, toluene, xylene, etc., and polar solvents such as acetonitrile, dichloromethane, acetone, chloroform, diethyl ether, tetrahydrofuran, dioxane, etc.

The reaction according to the present invention can be carried out at a temperature of from about 20° to about 150° C., preferably 40° to 120° C., for a period of from about 2 to about 50 hours, preferably from 8 to 40 hours.

The reaction of the present invention can be conducted in a pressure-resistant sealed vessel, e.g., in an autoclave, by charging the starting materials, the catalyst, the base and the solvent, if used, and then charging carbon monoxide to a predetermined pressure, and, after sealing the reaction vessel, heating the mixture, preferably with stirring.

Alternatively, in the process of this invention, the fluorine-containing alkyl halide represented by the formula (II) wherein $R^1$ represents a polyfluorocarbon group, one of $R^2$ and $R^3$ represents a hydrogen atom and the other of $R^2$ and $R^3$ represents a hydrogen atom, an alkyl group, or an aralkyl group can be formed in the reaction system in situ by using an olefine of the formula (IV)

wherein R represents a hydrogen atom, an alkyl group or an aralkyl group, and a polyfluoroalkyl halide of the formula (V)

wherein $R^1$ represents a polyfluorocarbon group and X represents an iodine atom, a bromine atom or a chlorine atom.

As described in T. Fuchikami and I. Ojima, *Tetrahedron Lett.*, Vol. 25, 303, 307 (1984), the above polyfluoroalkyl halide of the formula (V), in particular, that having a perfluoroalkyl group for $R^1$ and an iodine atom for X, easily undergoes an addition reaction to the above olefine of the formula (IV) in the presence of a catalyst of transition metal complex (e.g., a complex of Fe, Co, Ru, Pd, Ni, etc.) to form a compound represented by the formula (VI)

wherein R, $R^1$, $R^4$ and $R^5$ are as defined above, which corresponds to a starting material represented by the formula (II). Thus, the starting material of the formula (II) can be formed in situ in the reaction system from the compounds of formulae (IV) and (V).

The present invention is further illustrated in greater detail by the following Examples, but is not limited thereto. Unless otherwise indicated, all percents, parts, ratios and the like are by weight. In Examples, the symbols "Me", "Et", "Bu" and "Ph" stand for a methyl group, an ethyl group, a butyl group and a phenyl group, respectively.

EXAMPLE 1

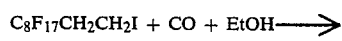

A 30 ml stainless steel autoclave was charged with dichlorobis(triphenylphosphine)palladium [$(Ph_3P)_2PdCl_2$] (14.4 mg, 0.02 mmol), 1-perfluorooctyl-2-iodoethane (0.288 g, 0.50 mmol) and $Et_3N$ (70 μl, 0.50 mmol), and, after carbon monoxide was charged into the autoclave at 30 atms., the mixture was reacted at 80° C. for 40 hours. The reaction mixture was extracted with hexane, and the extract was washed with water and dried over magnesium sulfate. The solvent was distilled off, and the resulting residue was subjected to isolation and purification by silica gel column chromatography to recover 14% 1-perfluoro-2-iodoethane and to obtain ethyl 3-perfluorooctylpropionate in a yield of 74% (86% conversion yield).

IR (neat)$\nu_{C=O}$: 1745 cm$^{-1}$; $^1$H-NHR (CDCl$_3$, TMS)δ: 1.28 (3H, t, J=7 Hz), 2.2–2.8 (4H, br), 4.18 (2H, q, J=7 Hz).

EXAMPLE 2

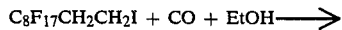

A 20 ml stainless steel autoclave was charged with $C_8F_{17}CH_2CH_2I$ (0.574 g, 1 mmol), $Co_2(CO)_8$ (34 mg, 0.1 mmol), EtOH (3 ml) and $Et_3N$ (0.127 ml, 0.9 mmol), and, after carbon monoxide was charged into the autoclave at 50 atms., the mixture was stirred at 100° C. for 24 hours. The reaction mixture was extracted with diethyl ether, washed with water and dried over magnesium sulfate. The solvent was distilled off under reduced pressure, and the resulting residue was isolated and purified by silica gel column chromatography to obtain 0.286 g (55% yield) of ethyl 3-perfluorooctylpropionate.

EXAMPLE 3

A 30 ml stainless steel autoclave was charged with $C_6F_{13}CH_2CH_2I$ (0.268 ml, 1 mmol), $(Ph_3P)_2PdCl_2$ (35.5 mg, 0.05 mmol), $Et_3N$ (0.14 ml, 1 mmol) and (i)BuOH (2 ml), and, after carbon monoxide was charged into the autoclave at 30 atms., the mixture was reacted at 100° C. for 24 hours. The reaction mixture was isolated and purified by silica gel column chromatography to obtain 0.19 g (42% yield) of isobutyl 3-perfluorohexylpropionate.

IR (neat) $\nu_{C=O}$: 1735 cm$^{-1}$. $^1$H-NMR (CDCl$_3$, TMS) δ: 0.93 (6H, d, J=7 Hz), 1.97 (1H, sep, J=7 Hz), 2.23–2.9 (4H, br), 3.94 (2H, d, J=7 Hz)

EXAMPLE 4

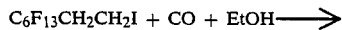

The reaction was conducted in the same manner as described in Example 3, except that EtOH (2 ml) was used instead of (i)BuOH used in Example 3, and 0.24 g (57% yield) of ethyl 3-perfluorohexylpropionate was obtained.

IR (neat) $\nu_{C=O}$: 1740 cm$^{-1}$. $^1$H-NMR (CDCl$_3$, TMS) δ: 1.27 (3H, t, J=7 Hz), 2.1–3.0 (4H, br), 4.2 (2H, q, J=7 Hz).

EXAMPLE 5

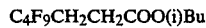

The reaction was conducted in the same manner as described in Example 3, except that C$_4$F$_9$CH$_2$CH$_2$I (0.192 ml, 1 mmol) was used instead of C$_6$F$_{13}$CH$_2$CH$_2$I used in Example 3, and 0.163 g (47% yield) of isobutyl 3-perfluorobutylpropionate was obtained.

IR (neat) $\nu_{C=O}$: 1740 cm$^{-1}$. $^1$H-NMR (CDCl$_3$, TMS) δ: 0.93 (6H, d, J=7 Hz), 1.97 (1H, sept, J=7 Hz), 2.22–3.0 (4H, br), 3.93 (2H, d, J=7 Hz).

EXAMPLE 6

The reaction was conducted in the same manner as described in Example 5, except that (n)BuOH (0.91 ml, 9.9 mmol) and heptane (0.09 ml) were used instead of (i)BuOH used in Example 5, and 0.15 g (44% yield) of butyl 3-perfluorobutylpropionate was obtained.

IR (neat) $\nu_{C=O}$: 1740 cm$^{-1}$. $^1$H-NMR (CDCl$_3$, TMS) δ: 0.95 (3H, t, J=7.2 Hz), 1.13–2.0 (4H, m), 2.1–2.9 (4H, br), 4.17 (2H, t, J=7 Hz).

EXAMPLE 7

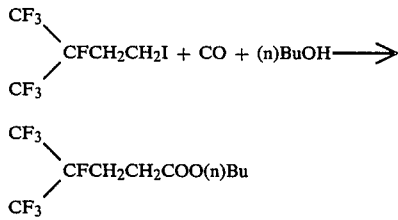

The reaction was conducted in the same manner as described in Example 3, except that (CF$_3$)$_2$CFCH$_2$CH$_2$I (0.168 ml, 1 mmol) was used instead of C$_6$F$_{13}$CH$_2$CH$_2$I and (n)BuOH (2 ml) was used instead of (i)BuOH used in Example 3, and 0.104 g (35% yield) of butyl 3-perfluoroisopropylpropionate was obtained.

IR (neat) $\nu_{C=O}$: 1740 cm$^{-1}$. $^1$H-NMR (CDCl$_3$, TMS) δ: 0.94 (3H, t, J=7.2 Hz), 1.1–1.9 (4H, br), 2.2–2.9 (4H, br), 4.15 (2H, t, J=7.2 Hz).

EXAMPLE 8

A 20 ml stainless steel autoclave was charged with (Ph$_3$P)$_2$PdCl$_2$ (34.7 mg, 0.05 mmol), CF$_3$CH$_2$CH$_2$I (56 μl, 0.5 mmol), Et$_3$N (70 μl, 0.50 mmol) and EtOH (1 ml), and, after carbon monoxide was charged into the autoclave at 50 atms., the mixture was stirred at 120° C. for 24 hours. The reaction mixture was quantitatively analyzed by gas chromatography and found that ethyl 4,4,4-trifluorobutylate was produced in 93% yield.

EXAMPLE 9

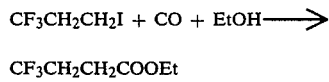

The reaction was conducted in the same manner as described in Example 8, except that Co$_2$(CO)$_8$ (17.1 mg, 0.05 mmol) was used instead of (Ph$_3$P)$_2$PdCl$_2$ and the reaction temperature of 120° C. was used instead of 100° C. used in Example 8, and ethyl 4,4,4-trifluorobutylate was obtained in a yield of 65%.

EXAMPLE 10

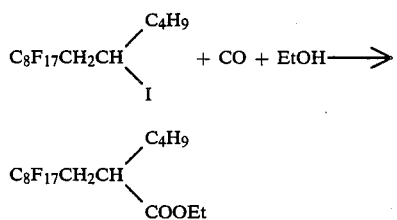

A 30 ml of stainless steel autoclave was charged with (Ph$_3$P)$_2$PdCl$_2$ (34.8 mg, 0.05 mmol), C$_8$F$_{17}$CHhd 2CH(C$_4$H$_9$)I (360 μl, 1 mmol), Et$_3$N (0.14 ml, 1.0 mmol) and EtOH (1 ml), and, after carbon monoxide was charged into the autoclave at 30 atms, the mixture was stirred at 80° C. for 12 hours. The reaction mixture was isolated and purified by silica gel column chromatography to obtain 0.43 g (75% yield) of ethyl 2-butyl-3-perfluorooctylpropionate.

$^1$H-NMR (CDCl$_3$, TMS) δ: 0.90 (3H, t, J=7 Hz), 1.27 (3H, t, J=7 Hz), 1.32 (4H, m), 1.58 (1H, m), 1.70 (1H, m), 2.12 (1H, m), 2.68 (1H, m), 2.78 (1H, m), 4.18 (3H, q, J=7 Hz).

EXAMPLE 11

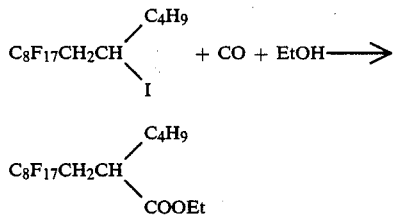

The reaction was conducted in the same manner as described in Example 10, except that a mixture of EtOH (0.6 ml) and heptane (0.4 ml) was used instead of EtOH (1 ml) used in Example 10, and 0.423 g (73% yield) of ethyl 2-butyl-3-perfluorooctylpropionate was obtained.

EXAMPLE 12

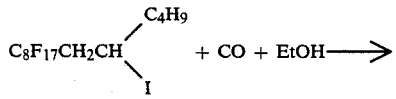

-continued

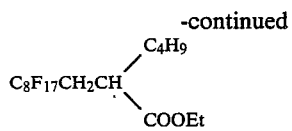

The reaction was conducted in the same manner as described in Example 11, except that dichloro(1,4-bisdiphenylphosphinobutane)palladium (30.4 mg, 0.05 mmol) was used instead of $(Ph_3P)_2PdCl_2$ used in Example 11, and 0.323 g (56% yield) of ethyl 2-butyl-3-perfluorooctylpropionate was obtained.

EXAMPLE 13

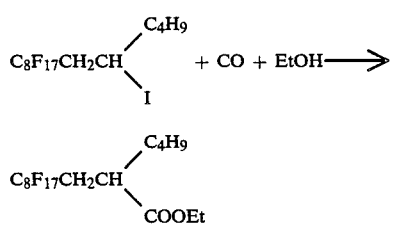

The reaction was conducted in the same manner as described in Example 11, except that dichloro(1,2-bisdiphenylphosphinoethane)palladium (29.1 mg, 0.05 mmol) was used instead of $(Ph_3P)_2PdCl_2$ used in Example 11, and 0.326 g (57% yield) of ethyl 2-butyl-3-perfluorooctylpropionate was obtained.

EXAMPLE 14

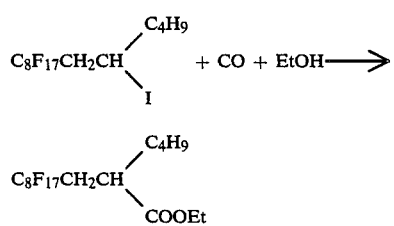

The reaction was conducted in the same manner as described in Example 11, except that dichloro(1,1'-bisdiphenylphosphinoferrocene)palladium (36.7 mg, 0.05 mmol) was used instead of $(Ph_3P)_2PdCl_2$, and 0.476 (83% yield) of ethyl 2-butyl-3-perfluorooctylpropionate was obtained.

EXAMPLE 15

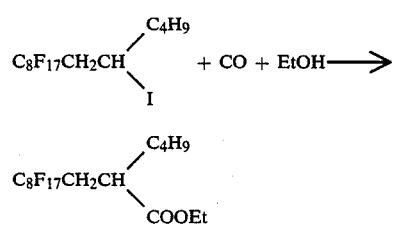

The reaction was conducted in the same manner as described in Example 11, except for using dichloro(1,3-bisdiphenylphosphinopropane)palladium (29.9 mg, 0.05 mmol) instead of $(Ph_3P)_2PdCl_2$ used in Example 11, and 0.312 g (54% yield) of ethyl 2-butyl-3-perfluorooctylpropionate was obtained.

EXAMPLE 16

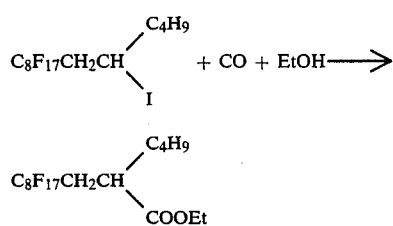

The reaction was conducted in the same manner as described in Example 11, except that $RhCl(PPh_3)_3$ (46.2 mg, 0.05 mmol) was used instead of $(Ph_3P)_2PdCl_2$ used in Example 11, and 0.275 g (48% yield) of ethyl 2-butyl-perfluorooctylpropionate was obtained.

EXAMPLE 17

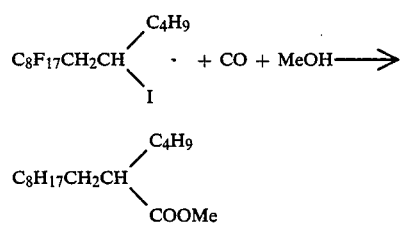

The reaction was conducted in the same manner as described in Example 10, except that a mixture of methanol (0.4 ml) and heptane (0.6 ml) was used instead of EtOH (1 ml) used in Example 10, and 0.356 g (68% yield) of methyl 2-butyl-3-perfluorooctylpropionate was obtained.

IR (neat) $\nu_{C=O}$: 1745 cm$^{-1}$. $^1$H-NMR (CDCl$_3$, TMS) δ: 0.9 (3H, t, J=7 Hz), 1.1-1.9 (6H, m), 1.93-3.0 (3H, m), 3.75 (3H, s).

EXAMPLE 18

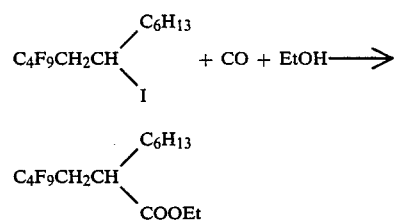

The reaction was conducted in the same manner as described in Example 10, except that $C_4F_9CH_2CH(C_6H_{13})I$ (0.30 ml, 1 mmol) was used instead of $C_8F_{17}CH_2CH(C_4H_9)I$ used in Example 10, and 0.22 g (54% yield) of ethyl 2-hexyl3-perfluorobutylpropionate was obtained.

IR (neat) $\nu_{C=O}$: 1735 cm$^{-1}$. $^1$H-NMR (CDCl$_3$, TMS) δ: 0.9 (3H, br), 1.27 (13H, br), 1.9-3.0 (3H, m), 4.22 (2H, q, J=7.2 Hz).

EXAMPLE 19

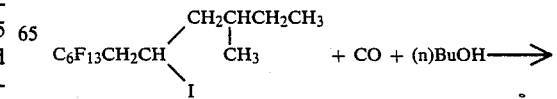

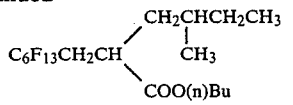

The reaction was conducted in the same manner as descrbied in Example 18, except that C₆F₁₃CH₂CH(I)CH₂CH(CH₃)CH₂CH₃ (0.328 ml, 1 mmol) and (n)BuOH were used instead of C₄F₉CH₂CH(C₆H₁₃)I and EtOH used in Example 18, and 0.24 g (46% yield) of butyl 2-(2-methylbutyl)-3-perfluorohexylpropionate.

IR (neat) $\nu_{C=O}$: 1745 cm⁻¹. ¹H-NMR (CDCl₃, TMS) δ: 0.93 (9H, br), 1.1-2.1 (9H, br), 2.1-3.1 (3H, m), 4.13 (2H, t, J=7 Hz).

EXAMPLE 20

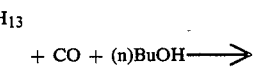
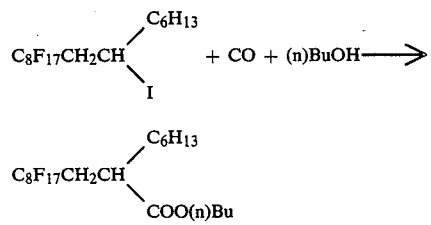

The reaction was conducted in the same manner as described in Example 19, except that C₈F₁₇CH₂CH(C₆H₁₃)I (0.394 ml, 1 mmol) was used instead of C₆F₁₃CH₂CH(I)CH₂CH(CH₃)CH₂CH₃ used in Example 19, and 0.34 g (54% yield) of butyl 2-hexyl-3-perfluorooctylpropionate was obtained.

IR (neat) $\nu_{C=O}$: 1735 cm⁻¹. ¹H-NMR (CDCl₃, TMS) δ: 0.93 (6H, br), 1.3 (14H, br), 1.9-3.0 (3H, m), 4.14 (2H, t, J=7 Hz).

EXAMPLE 21

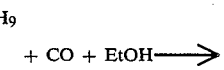
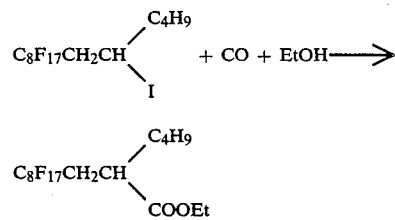

A 30 ml stainless steel autoclave was charged with (Ph₃P)₂PdCl₂ (4.1 mg, 0.0065 mmol), potassium carbonate (36.1 mg, 0.26 mmol), 1-perfluorooctyl-2-iodohexane (40 μl) and ethanol (0.5 ml), and, after carbon monoxide was charged into the autoclave at 10 atms., the mixture was reacted at 80° C. for 12 hours to obtain ethyl 2-butyl-3-perfluorooctylpropionate in 47% yield.

¹H-NMR (CDCl₃, TMS) δ: 0.90 (3H, t, J=7 Hz), 1.27 (3H, t, J=7 Hz), 1.32 (4H, m), 1.58 (1H, m), 1.70 (1H, m), 2.12 (1H, m), 2.68 (1H, m), 2.78 (1H, m), 4.18 (3H, q, J=7 Hz).

EXAMPLE 22

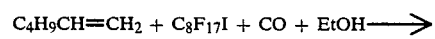

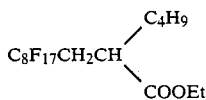

A 30 ml of stainless steel autoclave was charged with dichlorobis(triphenylphosphine)palladium (12.6 mg, 0.017 mmol), potassium carbonate (73.2 mg, 0.52 mmol), ethanol (1 ml), 1-hexene (108 μl, 0.86 mmol) and C₈F₁₇I (132 μl, 0.50 mmol), and, after carbon monoxide was charged into the autoclave at 30 atms., the mixture was reacted at 80° C. for 12 hours. The reaction mixture was extracted with n-hexane, washed with water and dried over magnesium sulfate. The solvent was distilled off under reduced pressure. The quantitative analysis of the resulting residue showed that ethyl 2-butyl-3-perfluorooctylpropionate was produced in 67% yield.

EXAMPLE 23

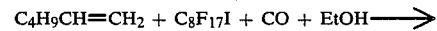

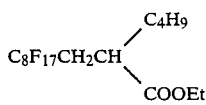

The reaction was conducted in the same manner as described in Example 22, except that dichlorobis(triphenylphosphine)platinum was used instead of dichlorobis(triphenylphosphine)palladium used in Example 22, and ethyl 2-butyl-3-perfluorooctylpropionate was obtained in 39% yield.

EXAMPLE 24

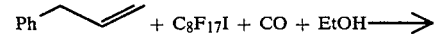

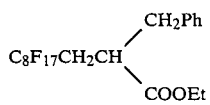

A stainless steel autoclave was charged with (Ph₃P)₂PdCl₂ (13.9 mg, 0.019 mmol), ethanol (1.5 ml), allylbenzene (131 μl, 1 mmol), C₈F₁₇I (132 μl, 0.50 mmol) and triethylamine (70 μl, 0.50 mmol), and carbon monoxide was charged into the autoclave at 30 atms. The mixture was then reacted at 80° C. for 24 hours to obtain ethyl 2-benzyl-3-perfluorooctylpropionate in 37% yield.

IR (neat) $\nu_{C=O}$: 1742 cm⁻¹. ¹H-NMR (CDCl₃, TMS) δ: 1.16 (3H, t, J=7 Hz), 1.87-3.27 (5H, br), 4.13 (2H, q, J=7 Hz), 7.3 (5H, m).

While the invention has been described in detail with reference to specific embodiments thereof, it will be apparent to one skilled in the art that various changes and modifications can be made therein without departing from the spirit and scope of the invention.

What is claimed is:

1. In a process for preparing a fluorine-containing carboxylic acid ester represented by the formula (I)

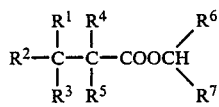  (I)

  (II)

wherein $R^1$ represents a fluorine atom or a polyfluoro alkyl group, $R^2$ and $R^3$ each represents a hydrogen atom, a fluorine atom, an alkyl group, an aralkyl group, an alkenyl group or an aryl group, $R^4$, $R^5$, $R^6$ and $R^7$ each represents a hydrogen atom, an alkyl group, an aralkyl group, an alkenyl group or an aryl group, and $R^2$ and $R^3$, $R^2$ and $R^4$, $R^3$ and $R^5$, $R^4$ and $R^5$, or $R^6$ and $R^7$, when taken together with the carbon atom(s) to which they are attached, can form a ring, in which a fluorine-containing compound is reacted with carbon monoxide and an alcohol of the formula (III)

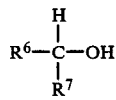  (III)

wherein $R^6$ and $R^7$ are as defined above, in the presence of a transition metal catalyst of the group VIII of the Periodic Table, the improvement which comprises employing as said fluorine-containing compound a fluorine-containing alkyl halide represented by the formula (II)

wherein $R^1$, $R^2$, $R^3$, $R^4$ and $R^5$ are as defined above, and X represents an iodine atom, a bromine atom or a chlorine atom, in the presence of a base in an amount of from about 0.5 to about 5 molar equivalent to the fluorine-containing alkyl halide of the formula (II), wherein said alcohol is used in an amount of at least an equimolar amount to the halide represented by the formula (II), and the reaction is carried out at a temperature of from about 20° to about 150° C.

2. A process as claimed in claim 1, wherein said reaction is conducted in a sealed vessel at a temperature of from about 20° to about 150° C.

3. A process as claimed in claim 1, wherein said transition metal catalyst is a metal of iron, ruthenium, osmium, cobalt, rhodium, iridium, nickel, palladium or platinum, or a metal compound thereof.

4. A process as claimed in claim 1, wherein said transition metal catalyst is used in an amount of from about 1/10000 to about 1/5 molar equivalent to the fluorine-containing alkyl halide of the formula (II).

5. A process as claimed in claim 1, wherein said reaction is conducted in the presence of an inert solvent.

6. The process of claim 1, wherein the carbon monoxide partial pressure is below about 50 atmospheres.

* * * * *